US009273049B2

(12) United States Patent
Liebenberg et al.

(10) Patent No.: US 9,273,049 B2
(45) Date of Patent: Mar. 1, 2016

(54) METHOD FOR INCREASING THE SOLUBILITY OF NEVIRAPINE

(75) Inventors: Wilna Liebenberg, Potchefstroom (ZA); Nicole Stieger, Potchefstroom (ZA)

(73) Assignee: North-West University (ZA)

( * ) Notice: Subject to any disclaimer, the term of this patent is extended or adjusted under 35 U.S.C. 154(b) by 0 days.

(21) Appl. No.: 13/509,216

(22) PCT Filed: Nov. 9, 2010

(86) PCT No.: PCT/IB2010/055077
§ 371 (c)(1),
(2), (4) Date: Oct. 31, 2012

(87) PCT Pub. No.: WO2011/058498
PCT Pub. Date: May 19, 2011

(65) Prior Publication Data
US 2013/0039987 A1    Feb. 14, 2013

(30) Foreign Application Priority Data

Nov. 10, 2009 (ZA) .................................. 2009/07879

(51) Int. Cl.
*A61K 9/00* (2006.01)
*C07D 471/14* (2006.01)

(52) U.S. Cl.
CPC ......... *C07D 471/14* (2013.01); *Y10T 428/2982* (2015.01)

(58) Field of Classification Search
None
See application file for complete search history.

(56) References Cited

U.S. PATENT DOCUMENTS

| 4,132,848 | A  | * | 1/1979 | Cise et al. ..................... 540/228 |
| 7,083,680 | B2 | * | 8/2006 | Hamada ......................... 117/104 |
| 2005/0059653 | A1 |   | 3/2005 | Reguri et al. |
| 2009/0169620 | A1 | * | 7/2009 | Venkatesh et al. ............ 424/464 |

FOREIGN PATENT DOCUMENTS

| WO | WO 9909990 A1 | * | 3/1999 |
| WO | WO-9909990 A1 |   | 3/1999 |
| WO | WO 2008103899 A1 | * | 8/2008 |
| WO | WO-2008103899 A1 |   | 8/2008 |
| WO | WO-2011058498 A2 |   | 5/2011 |
| WO | WO-2011058498 A3 |   | 5/2011 |
| WO | WO 2011073907 A1 | * | 6/2011 |

OTHER PUBLICATIONS

Kettner ey al. Selective crystallization of indigo B by a modified sublimation method and its redetermined structure. Acta Cryst. (2011). E67, o2867-sup8 (and references therein).*
Wagner et al. Purification and characterization of phthalocyanines. Journal of Materials Science 17 (1982):2781-2791.*
Wagner et al. Purification and characterization of phthalocyanines. Journal of Materials Science 17 (1982) 2781-2791.*
Liebenberg et al. Nevirapine Micro-Spheres. (http://www.flintbox.com/public/project/5143/ posten online Aug. 5, 2010).*
Stieger et al. Recrystallization of Active Pharmaceutical Ingredients. In Crystallization: Science and Technology; Andreeta, M. R. B., Ed.; InTech: Rijeka, Croatia, 2012; Chapter 7, pp. 183-204.*
"International Application Serial No. PCT/IB2010/055077, Int'l Preliminary Report on Patentability mailed Mar. 13, 2012", 17 pgs.
"International Application Serial No. PCT/IB2010/055077, International Search Report mailed Jul. 20, 2011", 6 pgs.
"Neviapine Micro-Spheres", [Online]. Retrieved from the Internet: <URL: http://www.flintbox.com/public/project/5143> Retrieved Jun. 5, 2011, (Aug. 5, 2010), 2 pgs.
Caira, Mino, et al., "Solvent Inclusion by the Anti-HIV Drug Nevirapine: X-Ray Structures and Thermal Decomposition of Representative Solvates", Cryst. Growth Des., 8 (1), (2008), 17-23.
Rasenack, N, et al., "Dissolution rate enhancement by in situ micronization of poorly water-soluble drugs", Pharm Res., 19(12), (Dec. 2002), 1894-900.

* cited by examiner

*Primary Examiner* — Robert A Wax
*Assistant Examiner* — Olga V Tcherkasskaya
(74) *Attorney, Agent, or Firm* — Schwegman Lundberg & Woessner, P.A.

(57) ABSTRACT

The invention provides a method for increasing the solubility of nevirapine, including the steps of rendering nevirapine in a gaseous phase; and rendering the gaseous phase in a relatively more soluble solid particulate form. The invention further provides for a crystalline Form-VI (36) of nevirapine having an X-ray diffraction pattern of (2-theta values in degrees) 9.2953, 11.2023, 12.7019, 12.9796, 13.5273, 15.4670, 17.2597, 19.1038, 19.7267, 21.1303, 22.9381, 25.5589, 26.4913, 27.2150, 27.7283, 29.7134, and 33.8343 degrees two theta. The invention further provides for the preparation of microspherical and/or nanospherical Form-V (34) and crystalline Form-VI (36) of nevirapine as well as novel dosage forms including parenteral-, inhalant-, transdermal- and oral dosage forms.

13 Claims, 6 Drawing Sheets

METHOD FOR INCREASING THE SOLUBILITY OF NEVIRAPINE

RELATED APPLICATION

This application is a nationalization under 35 U.S.C. 371 of PCT/IB2010/055077, filed Nov. 9, 2010 and published as WO 2011/058498 A2 on May 19, 2011, which claimed priority under 35 U.S.C. 119 to South African Patent Application Serial No. 2009/07879, filed Nov. 10, 2009; which applications and publication are incorporated herein by reference and made a part hereof.

BACKGROUND TO THE INVENTION

This invention relates to method for increasing the solubility of a transcriptase inhibitor composition and a transcriptase inhibitor composition prepared in accordance with such a method. More particularly, but not exclusively, this invention relates to a method for increasing the solubility of nevirapine to increase the bioavailability and efficacy thereof. This invention further relates to new forms of nevirapine.

The present invention further relates to novel crystalline forms of 11-cyclopropyl-5,11-dihydro-4-methyl-6H-dipyrido[3,2-b: 2',3'-e][1,4]diazepin-6-one, generically known as nevirapine. More specifically, the present invention provides novel microspherical and/or nanospherical Form-V and crystalline Form-VI of nevirapine.

Nevirapine is a well-known anti-retroviral drug used in the treatment of HIV-1 infection and AIDS. It is a non-nucleoside reverse transcriptase inhibitor and, structurally, it is a member of the dipyridodiazepinone chemical class of compounds.

A first disadvantage experienced with commercially available nevirapine is that it is highly hydrophobic and very poorly water soluble. Although comprehensive solubility and permeability data for nevirapine is lacking, the FDA classifies nevirapine as a Class II (high permeability, low solubility) drug. nevirapine's water solubility at neutral pH is ~1 mg/ml, and is only highly soluble at pH<3.

Nevirapine is currently available in two dosage forms, namely tablets (anhydrous form) and in suspensions (hemihydrate form). The mean maximum particle sizes of commercially available nevirapine are generally larger than 50 µm.

A further disadvantage experienced with nevirapine is that there are no parenteral dosage forms available, because of the relatively large particle size and poor water solubility. Particle sizes of commercially available nevirapine raw materials are unsuitable for parenteral administration in suspension. Further owing to the particle sizes, nevirapine in inhalant and transdermal dosage forms are also not available.

Yet another disadvantage experienced with known forms of nevirapine is that bioavailability thereof decreases at higher doses due to absorption being solubility rate-limited.

US patent application number 2005/0059653 describes crystalline Form-II and Form-III of nevirapine. A disadvantage of both these forms is that they are also suffering from poor solubility.

Applicant is the co-applicant of a separate patent application in respect of another form of nevirapine, namely Form-IV. The novel forms of nevirapine referred to herein are thus designated Form-V and Form-VI respectively.

SUMMARY OF THE INVENTION

The object of the invention is to provide novel forms of nevirapine. Another object of the invention is to provide a method for increasing the solubility of a transcriptase inhibitor composition. Yet another object of the invention is to provide a medicament and dosage forms prepared in accordance with such a method with which the aforesaid disadvantages may be overcome or at least minimised.

According to the first aspect of the invention there is provided a crystalline Form-VI of nevirapine having an X-ray diffraction pattern of (2-theta values in degrees) 9.2953, 11.2023, 12.7019, 12.9796, 13.5273, 15.4670, 17.2597, 19.1038, 19.7267, 21.1303, 22.9381, 25.5589, 26.4913, 27.2150, 27.7283, 29.7134, and 33.8343 degrees two theta.

The crystalline Form-VI of nevirapine may have an X-ray powder diffraction pattern of at least 25% similarity to the X-ray diffraction pattern depicted in FIG. 7.

Preferably, the crystalline Form-VI of nevirapine has the X-ray powder diffraction pattern depicted in FIG. 7.

Further according to the invention the crystalline Form-VI of nevirapine is in a particulate form, wherein the particles have a mean maximum diameter of less than 50.0 µm.

The particles of crystalline Form-VI of nevirapine may have a mean maximum diameter of less than 4.0 µm, preferably between 0.1 to 4.0 µm.

The crystalline particles of the crystalline Form-VI of nevirapine may aggregate in the form of nanospheres and/or microspheres (Form-V).

The nanospheres and/or microspheres of the Form-V of nevirapine may be coated with a protective layer.

According to a second aspect of the invention there is provided a method for increasing the solubility of a transcriptase inhibitor composition, including the steps of:
  rendering the composition in a gaseous phase; and
  rendering the gaseous phase in a relatively more soluble solid particulate form.

Further according to the invention the transcriptase inhibitor composition is of the type that sublimes.

Further according to the invention, the step of rendering the composition in a gaseous phase includes the further steps of sublimating the composition and depositing the gaseous phase in a relatively more soluble solid particulate form onto a surface.

The step of allowing the composition to sublimate may include the further step of elevating the temperature of the composition. Preferably the temperature of the composition is increased to above 150 degrees Celsius at atmospheric pressure. Alternatively or in addition, the step may include the further step of subjecting the composition to sublimation at a pressure relatively lower than atmospheric pressure.

Alternatively, the step of rendering the composition in a gaseous phase may include the step of evaporating the composition.

Further according to the invention the step of rendering the gaseous phase in a relatively more soluble solid particulate form may include the step of depositing the composition onto a surface such that the particles have a mean maximum diameter of less than 50.0 μm.

Preferably, the composition is deposited in a solid particulate form such that the particles have a mean maximum diameter of less than 4.0 μm, further preferably between 0.1 to 4.0 μm.

Further according to the invention the composition is deposited in a crystalline form and the method includes the further step of allowing the crystalline particles to aggregate to form microspheres.

The method may include the further step of coating the microspheres with a protective layer.

Further according to the invention the transcriptase inhibitor is in the form of nevirapine.

According to a third aspect of the invention there is provided a transcriptase inhibitor composition prepared in accordance with the method of the second aspect of the invention.

The transcriptase inhibitor may be provided in a parenteral dosage form.

Alternatively, the transcriptase inhibitor may be provided in the form of an inhalant.

Further alternatively, the transcriptase inhibitor may be provided in an oral dosage form.

Yet further alternatively, the transcriptase inhibitor may be provided in a form suitable for transdermal administration.

According to the fourth aspect of the invention there is provided use of a transcriptase inhibitor composition, according to the first aspect of the invention and prepared in accordance with the method of the second aspect of the invention, in the preparation of a medicament for use in a method of treating a patient suffering from an immune deficiency condition.

According to the fifth aspect of the invention there is provided use of a transcriptase inhibitor composition, according to the first aspect of the invention and prepared in accordance with the method of the second aspect of the invention, in a method of treating a patient suffering from an immune deficiency condition, including the step of administering to such a patient a pharmaceutically effective amount of such composition.

BRIEF DESCRIPTION OF THE DRAWINGS

The invention will now be described further, by way of example only, with reference to the accompanying drawings wherein.

DESCRIPTION

Figure 1:
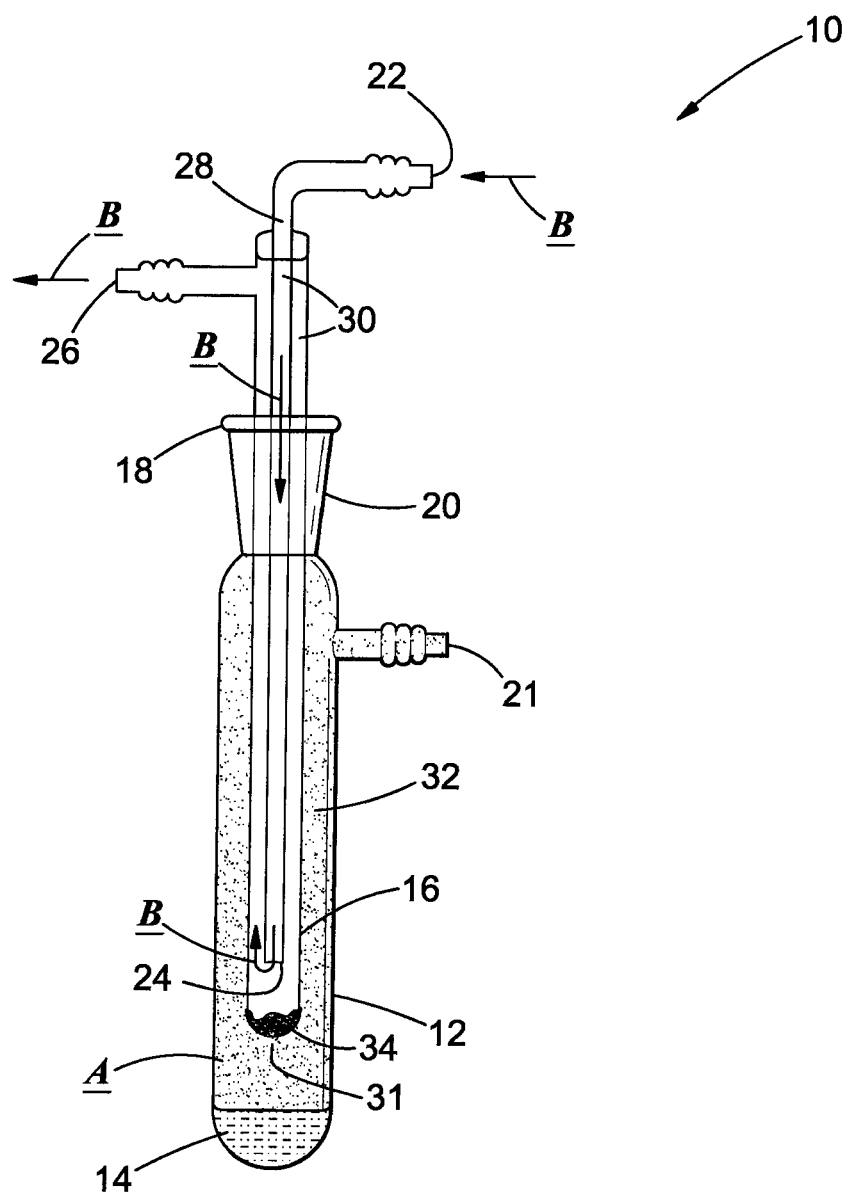
FIG. 1: is a diagrammatical representation of apparatus for preparing a medicament in accordance with a preferred embodiment of the invention on a non-commercial scale.
Figure 2:
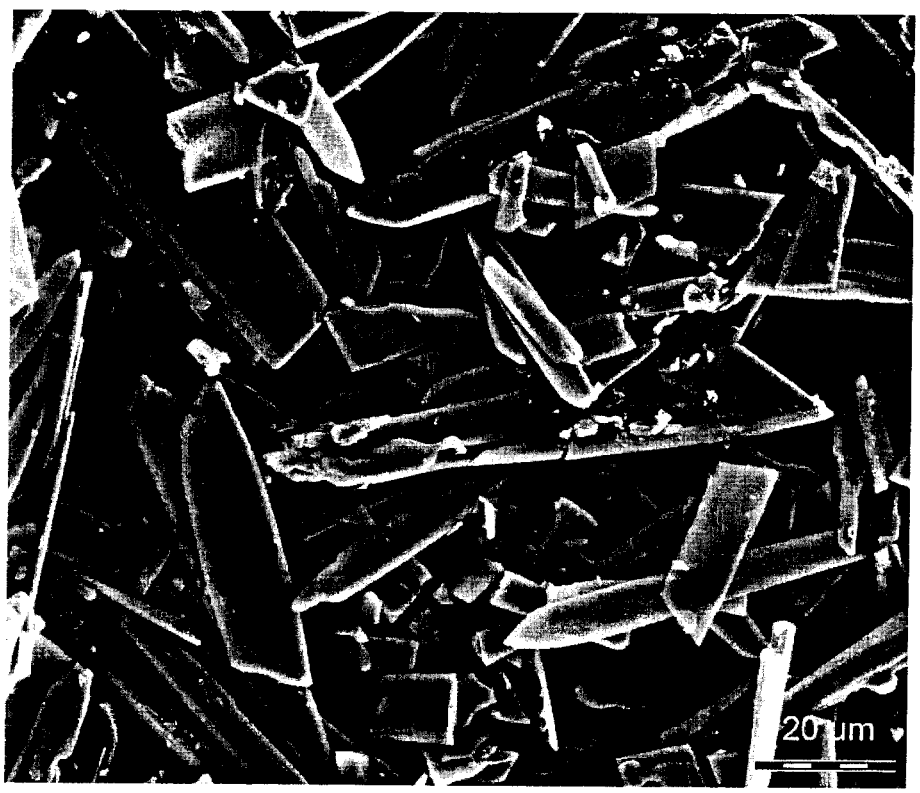
FIG. 2: is a Scanning Electron Microscope (SEM) photo of bladed crystals of anhydrous nevirapine recrystallised from 20:80 ethanol:water according to the prior art.
Figure 3:
FIG. 3: is a SEM photo of platy crystals of hemi-hydrate nevirapine recrystallised from 40:60 ethanol:water according to the prior art (STIEGER, N., et al. 2010. Influence of the Composition of Water/Ethanol Mixtures on the Solubility and Recrystallization of Nevirapine. *Crystal Growth & Design*, 10(9):3859-3868)

Referring to FIG. 1, apparatus for use in a method according to one aspect of the invention, for increasing the solubility of a transcriptase inhibitor composition that sublimes, is generally designated by numeral 10.

The apparatus 10 comprises a conventional sublimation finger which includes a tubular outer glass container 12 for containing a transcriptase inhibitor in the form of nevirapine 14. The apparatus 10 further includes a tubular inner glass container 16 disposed concentrically within the outer container 12.

The outer container 12 includes an upper mouth 18 (wherein the inner container 16 is flushly and sealingly received by means of a collar 20); and a port 21.

The inner container 16 is provided with an inlet tube 22 extending concentrically with the inner container 16 and providing an outlet opening 24 towards the lower end of the inner container 16. The inner container 16 is further provided with an outlet tube 26 towards an opposite upper end of the inner container 16. A passage 28 for coolant 30, such as water below 10 degrees Celsius, is thus defined by the inlet tube 22, the inner container 16 and the outlet tube 26. The inner container 16 further defines an outer condensation surface 31 disposed above the nevirapine 14.

In use, conventional nevirapine 14 in a solid anhydrous form is disposed in the bottom of the outer container 12 via the mouth 18 and heated to a temperature above 150 degrees Celsius. The nevirapine 14 sublimates into a gaseous phase 32 filling a sublimation zone A in the outer container 12 above the solid nevirapine 14. The said coolant 30 is simultaneously passed along the passage 28, as indicated by arrows B, to cool the inside of the inner container 16 and thus the outer condensation surface 31 thereof.

The condensation surface 31 is thus cooled whilst in contact with the gaseous phase 32 of the nevirapine in the sublimation zone A, so that the nevirapine in the gaseous phase 32 condensates and is thus deposited on the condensation surface 31 in solid particles in the form crystalline nevirapine (Form-VI).

In accordance with an alternative embodiment of the invention, the pressure inside the outer container 12 is reduced below atmospheric pressure, by connecting the inlet 21 to a vacuum pump (not shown). In doing so, the nevirapine 14 would commence sublimation at temperatures below 150 degrees Celsius, and, which the applicant foresees, could lead to a relatively higher yield of pharmaceutically active final product.

Figure 8:
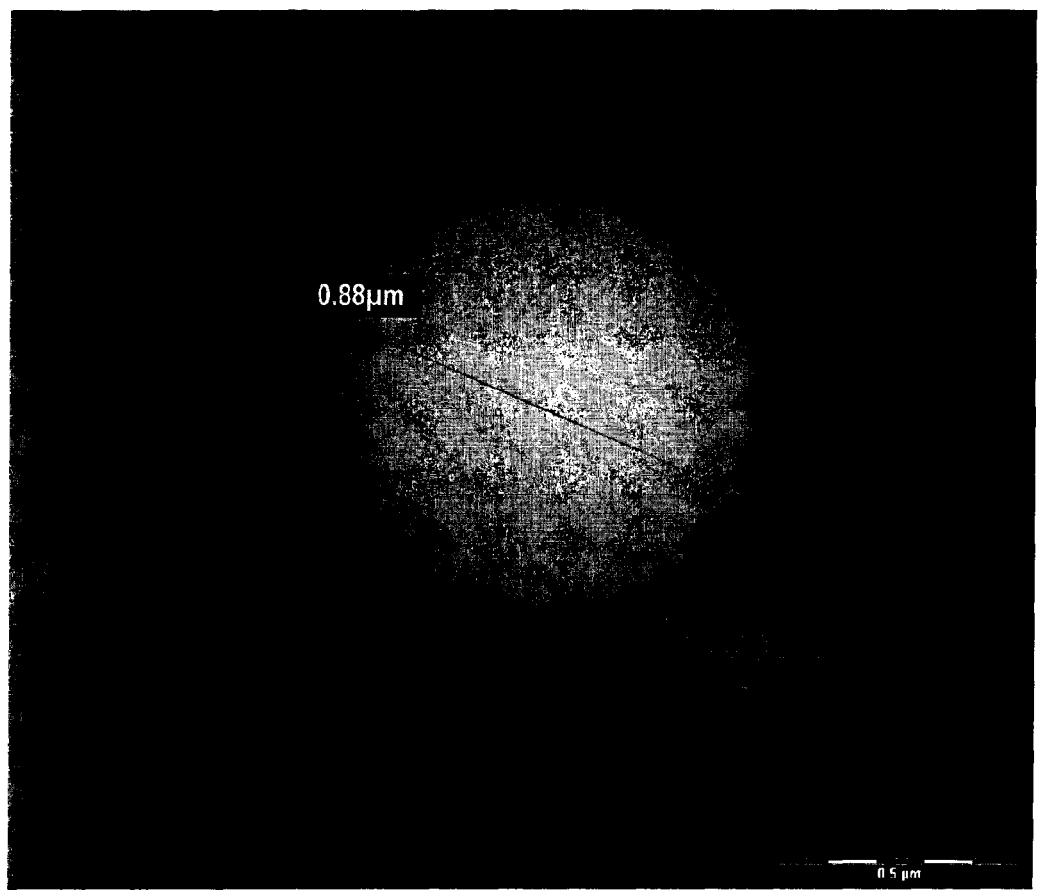
FIG. 8: is a SEM photo of the microspherical Form-V of nevirapine depicting the respective sizes of two particles as 0.17 and 0.88 µm.

Applicant has found that the nanospheres and microspheres 34 (Form-V) that form on the condensation surface 31 have a mean maximum diameter of less than 50 µm, which is substantially smaller than the mean maximum diameter of commercially available nevirapine. More specifically, it was found that the nanospheres and microspheres 34 have mean maximum diameters ranging between 0.1 to 4.0 µm. Applicant has found that by manipulating the production parameters, such as by reducing the temperature of the condensation surface 31 further, even smaller nanospheres having a mean maximum diameter of 0.17 and 0.88 µm are formed (as depicted in FIG. 8). The formation of microspheres and/or nanospheres unexpectedly substantially increases the water solubility and thus the bioavailability and efficacy thereof, relative to prior art anhydrous and hemi-hydrate forms of nevirapine. FT-IR analysis proved the final product to be nevirapine of a relatively very high chemical purity, and not a degradation product.

Figure 4:
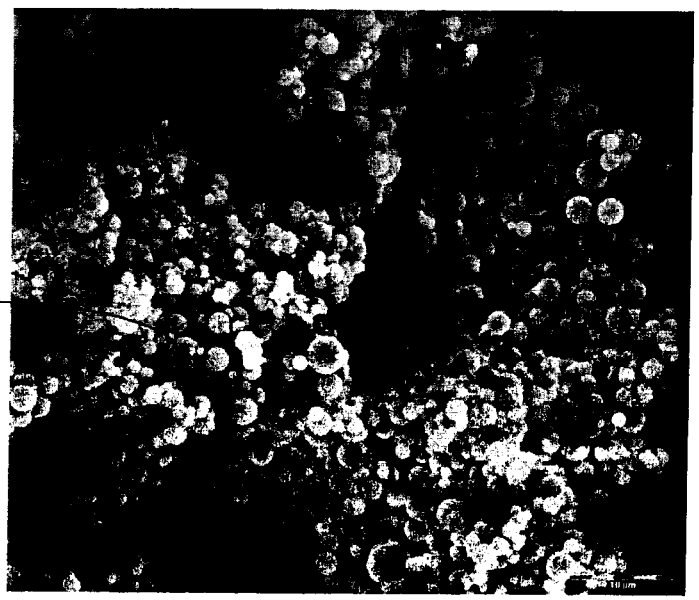
FIG. 4: is a SEM photo of microspherical novel Form-V of nevirapine prepared in accordance with the invention.
Figure 5:
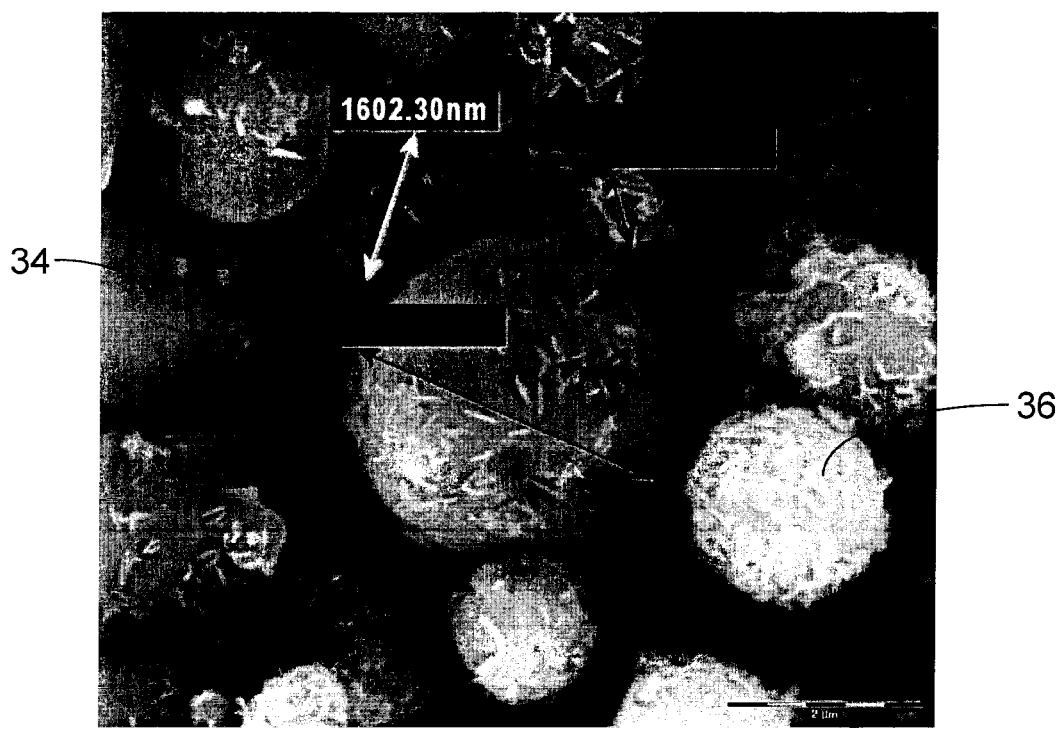
FIG. 5: is a SEM photo of microspherical novel Form-V of nevirapine prepared in accordance with the invention.

Applicant prepared SEM photos (FIGS. 4 and 5) showing crystalline nevirapine (Form-VI), aggregated into nanospheres and microspheres 34 (Form-V) with average sizes in the order of 0.1 µm to 4 µm. A preliminary solubility experiment showed the nanosphere and microsphere aggregation to be at least 30% more soluble than the conventional anhydrous form of nevirapine, and 140% more soluble than the conventional hemi-hydrate form.

Applicant further prepared a SEM photo (FIG. 8) of nanospheres (Form-V) with average sizes in the order of 0.17 and 0.88 µm.

It was further surprisingly observed, subject to the temperature of the condensation surface 31, that additional nanocrystals 36 (Form-VI) form on the surface of the nanospheres and microspheres 34 and that these nanocrystals, dependant on the preparation conditions also aggregate to form the nanospheres and/or microspheres. The nanospheres and/or microspheres tend to form an aggregate with one another and hence it is proposed to coat the nanospheres and/or microspheres with a protective coating shortly after formation, to limit such aggregation, thus to further increase the solubility and bioavailability thereof. Such a coating could be in the form of shellac or biocompatible water soluble polymer. Coating of the spheres with polymers or other biocompatible substances is used to limit the aggregation between spheres, to improve powder characteristics and to improve or prohibited solubility. Further application is to ensure pH-dependant solubility and targeted drug delivery, for example to the small intestines or colon.

The individual crystals 36 have individual mean maximum diameters that are substantially smaller than that of the nanospheres and microspheres 34. Thus, in accordance with a further step of the invention, crystal aggregates form of which the maximum mean diameters of the individual crystals 36 are less than 0.5 µm. It is expected that the nanocrystalline (Form-VI) of nevirapine would display an even further increase in water solubility and bioavailability/efficacy.

It is foreseen that various methods could be employed to remove the microspheres, nanospheres, or crystals as they are formed, to limit clustering or aggregation thereof.

It is further foreseen that instead of having a condensation surface 31, alternative collection methods could be employed such as collecting the gaseous phase in a liquid trap, alternatively with electrostatic charge or further alternatively by means of a vortex (all not shown).

Figure 6:
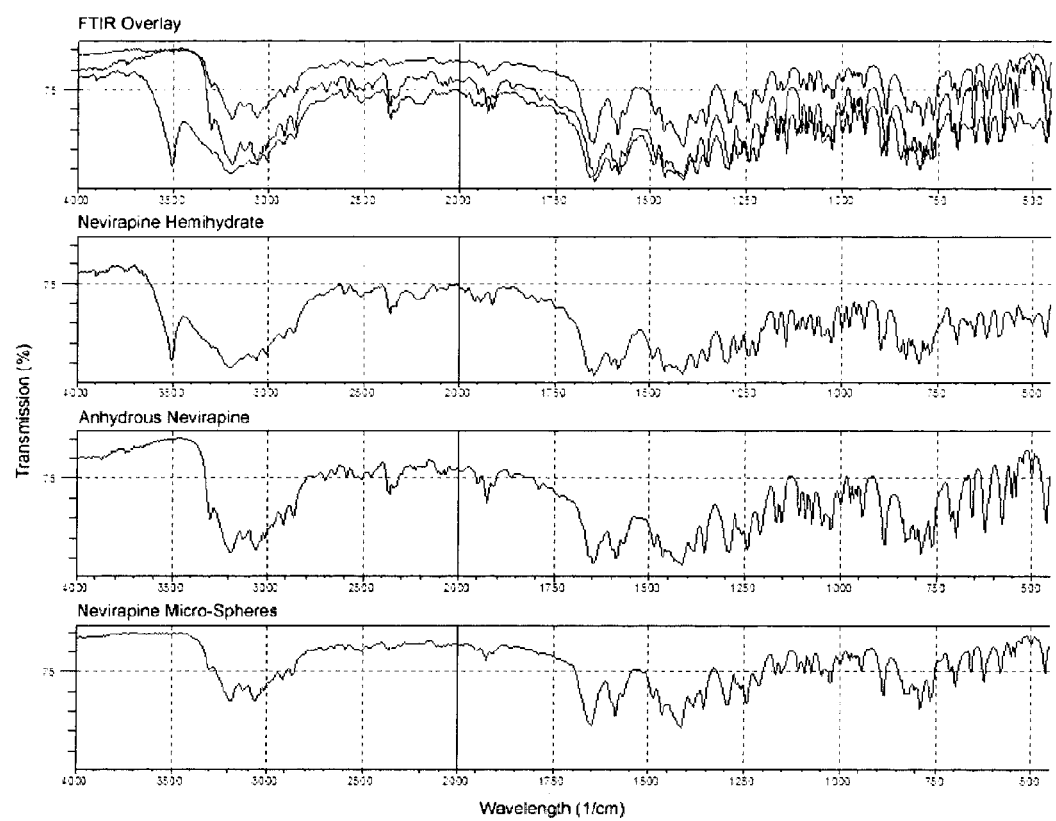
FIG. 6: is a graph depicting Fourier Transform Infrared Spectroscopy (FT-IR) traces of three forms of nevirapine, namely microspherical-, anhydrous and hemi-hydrate forms.

A FTIR overlay was prepared for comparing Form-V to two known commercially available forms of nevirapine (FIG. 6) namely anhydrous and hemihydrous nevirapine. FIG. 6 shows that the spectra of the microspheres 34 and the anhydrous form are similar. This is an indication that the microspheres 34 contain pure nevirapine and that no degradation took place during the preparation of nevirapine Form-V.

Figure 7:
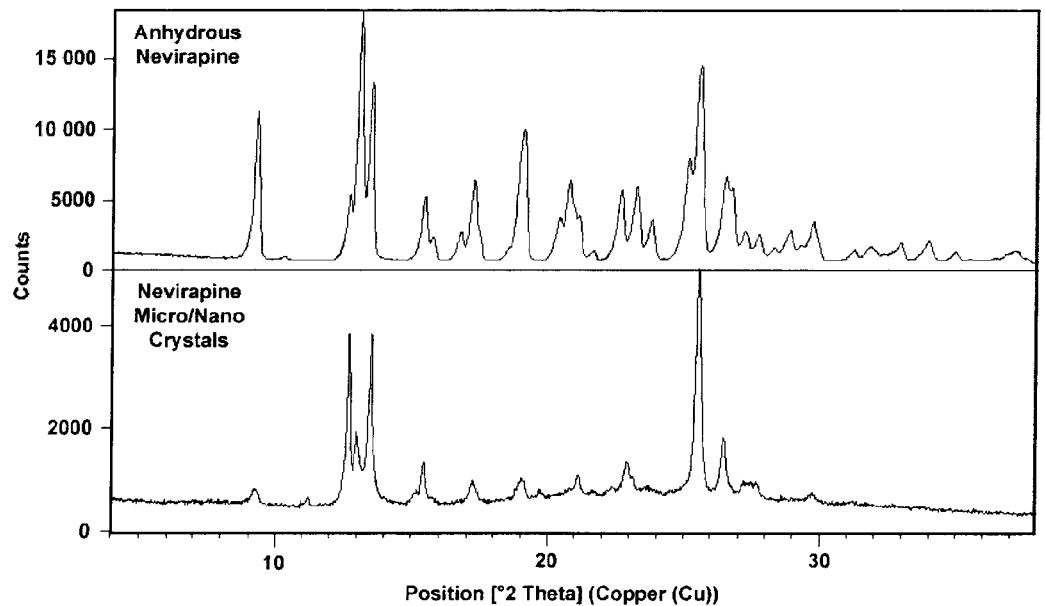
FIG. 7: is an X-ray power diffractometry (XRPD) overlay comparing regular anhydrous nevirapine to the crystalline Form-VI thereof.

Applicant further prepared an X-ray diffraction pattern of the crystals 36 and found that the crystals displayed the X-ray diffraction pattern depicted in FIG. 7.

It is foreseen that nevirapine in microspherical and nanospherical form (Form-V) or micro/nano-crystalline form (Form-VI) could present substantial advantages over prior art forms. For example, it was found that a method according to the invention renders the final product in a form suitable for administration in ways not previously possible. For example, the nevirapine in crystalline form could be administered to a patient suffering from an immune deficiency condition such as HIV infection or AIDS in a parenteral dosage form and, specifically, by way of injection. Alternatively, it could be administered in the form of an inhalant. Further alternatively, the medicament could be provided in an oral dosage form. Yet further alternatively, it could be provided in a form suitable for transdermal administration.

It will be appreciated that the apparatus 10 is suitable for preparing a medicament according to the invention merely on an experimental basis in a laboratory and that entirely different apparatus would have to be designed and developed for the production of a medicament according to the invention on a commercial or industrial scale. It is foreseen that the main elements for the successful production of the medicament of the invention are the elevation of temperature of the composition to establish an acceptable level of sublimation and the reduction of pressure in the sublimation zone, to expedite sublimation at relatively lower temperatures; and a surface having a temperature which is relatively lower than the temperature of the sublimation zone. In addition, it is foreseen that deposition of the composition from the gaseous phase could also be achieved by using a static charge; a vortex; or that the product may be collected in a liquid trap.

In the case of a liquid trap, the gaseous phase may be bubbled through a liquid in which nevirapine is poorly soluble. This liquid might be cooled to relatively lower temperature than the gaseous phase, so that the microspheres would form within the liquid.

In the case of using an electrostatic charge, the gaseous phase is attracted to a statically charged object (cooled or otherwise) to collect in particulate form.

In the case of a vortex, the gaseous phase is continually extracted by means of air/gas flow and collected in a receptacle with or without the use of baffles. The vortex could be combined with cooling to relatively lower temperature than the nevirapine gaseous phase.

It is also foreseen that the above methods could be used in various combinations.

It will be appreciated further that variations in detail are possible with the invention described herein without departing from the scope of the appended claims.

The invention claimed is:

1. A method for increasing the solubility of nevirapine, including the steps of rendering the nevirapine in a gaseous phase; and rendering the gaseous phase in a solid particulate form of crystallites having a mean maximum diameter of less than 4.0 µm and concomitantly aggregating the crystallites to form microspheres having a mean maximum diameter of less than 50 µm.

2. The method of claim 1 wherein the step of rendering the nevirapine in a gaseous phase includes the further steps of sublimating the nevirapine and wherein the step of rendering the gaseous phase in a solid particulate form includes the step of depositing the gaseous phase onto a surface.

3. The method of claim 2 wherein the step of sublimating the nevirapine includes the further step of elevating the temperature of the nevirapine.

4. The method of claim 3 wherein the step of elevating the temperature of the nevirapine includes the step of elevating the temperature to above 150 degrees Celsius at atmospheric pressure.

5. The method of claim 2 wherein the step of sublimating the nevirapine includes the step of subjecting the nevirapine to sublimation at a pressure lower than atmospheric pressure.

6. The method of claim 1 wherein the step of rendering the nevirapine in a gaseous phase includes the step of evaporating the nevirapine.

7. The method of claim 1 including the further step of coating the microspheres with a protective layer.

8. A crystalline form of nevirapine prepared with a method according to claim 1 in a dosage form selected from the group consisting of parenteral-; inhalant-; oral- and transdermal administration-dosage forms.

9. A novel form of nevirapine prepared with a method according to claim 1 comprising an aggregate of a plurality of particles of crystalline form of nevirapine.

10. A novel form of nevirapine according to claim 9, wherein the crystalline particles are aggregated in the form of nanospheres and/or microspheres.

11. A method to treat an immune deficiency condition comprising administering to a patient in need thereof an effective amount of nevirapine prepared in accordance with the method of claim 1.

12. The method of claim 1 wherein crystallites have a mean maximum diameter of between 0.1 μm to 4.0 μm.

13. The method of claim 1 wherein the step of forming the crystallites includes the step of elevating the temperature of the nevirapine and subjecting the nevirapine to sublimation at a pressure lower than atmospheric pressure.

* * * * *